United States Patent [19]
Heshmat

[11] Patent Number: 6,158,893
[45] Date of Patent: Dec. 12, 2000

[54] HIGH LOAD CAPACITY COMPLIANT FOIL HYDRODYNAMIC JOURNAL BEARING

[75] Inventor: Hooshang Heshmat, Niskayuna, N.Y.

[73] Assignee: Mohawk Innovative Technology, Inc., Albany, N.Y.

[21] Appl. No.: 09/447,460

[22] Filed: Nov. 22, 1999

Related U.S. Application Data

[62] Division of application No. 09/234,719, Jan. 21, 1999, Pat. No. 5,988,885, which is a division of application No. 08/827,203, Mar. 28, 1997, Pat. No. 5,902,049.

[51] Int. Cl.$^7$ ..................................................... F16C 17/03
[52] U.S. Cl. ............................................................. 384/106
[58] Field of Search .................................... 384/106, 103, 384/104, 105

[56] References Cited

U.S. PATENT DOCUMENTS

| | | |
|---|---|---|
| 3,809,443 | 5/1974 | Cherubim . |
| 4,229,054 | 10/1980 | Miller, Jr. . |
| 4,262,975 | 4/1981 | Heshmat et al. . |
| 4,274,683 | 6/1981 | Gray et al. . |
| 4,277,111 | 7/1981 | Gray et al. . |
| 4,277,112 | 7/1981 | Heshmat . |
| 4,277,113 | 7/1981 | Heshmat . |
| 4,295,689 | 10/1981 | Licht . |
| 4,296,976 | 10/1981 | Heshmat . |
| 4,300,806 | 11/1981 | Heshmat . |
| 4,415,281 | 11/1983 | Agrawal . |
| 4,435,839 | 3/1984 | Gu et al. . |
| 4,451,163 | 5/1984 | Glaser . |
| 4,465,384 | 8/1984 | Heshmat et al. . |
| 4,475,824 | 10/1984 | Glaser et al. . |
| 4,549,821 | 10/1985 | Kawakami . |
| 4,552,466 | 11/1985 | Warren . |
| 4,699,523 | 10/1987 | Hagemeister . |
| 4,950,089 | 8/1990 | Jones . |
| 5,110,220 | 5/1992 | Gu . |
| 5,116,143 | 5/1992 | Saville et al. . |
| 5,228,785 | 7/1993 | Saville et al. . |
| 5,248,205 | 9/1993 | Gu et al. . |
| 5,318,366 | 6/1994 | Nadjafi . |

OTHER PUBLICATIONS

H. Heshmat, "Analysis of Compliant Foil Bearings with Spatially Variable Stiffness", AIAA/SAE/ASME/ASEE 270 Joint Propulsion Conference, Jun. 24–26, 1991, pp. 1–11, Sacramento, CA.

H. Heshmat et al, "Application of Compliant Fluid–Film Bearings to the High–Pressure Oxygen Turbopump of the SSME", 1992 Conference on Advanced Earth–To–Orbit Propulsion Technology, May 19–21, 1992, pp. 1–10, Marshall Space Flight Center, Alabama.

H. Heshmat, "A Feasibility Study on the Use of Foil Bearings in Cryogenic Turbopumps", AIAA/SAE/ASME/ASEE 27$^{th}$ Joint Propulsion Conference, Jun. 24–26, 1991, pp. 1–12, Sacramento, CA.

H. Heshmat et al, "Development of Foil Journal Bearings for High Load Capacity and High Speed Whirl Stability," ASLE—ASME Joint Lubrication Conference; Oct. 4–7, 1981, pp. 1–8, New Orleans, LA.

(List continued on next page.)

*Primary Examiner*—Lenard A. Footland
*Attorney, Agent, or Firm*—Hodgson, Russ, Andrews, Woods, & Goodyear

[57] ABSTRACT

A compliant hydrodynamic fluid film journal bearing for handling high loads. The bearing assembly includes a first thin smooth compliant sheet for facing a shaft, one or more corrugated foils, and a second sheet between the foils and the compliant sheet for supportedly underlying the compliant sheet for preventing sagging of the first sheet between ridges of the foils. A foil element is anchored at a position intermediate its ends to the bearing sleeve whereby both ends thereof are unanchored. A pair of radially outer and inner corrugated foils have outer foil ridges which underlie some inner foil ridges and outer foil furrows which underlie others of the inner foil ridges. A bearing assembly includes a plurality of rows of corrugated foil elements wherein ends of foil elements are offset circumferentially from ends of foil elements in adjacent rows symmetrically from the radial centerplane to provide a herringbone pattern effect. At least some ridges on at least one of inner and outer corrugated foils have truncated apex portions.

2 Claims, 8 Drawing Sheets

U.S. PATENT DOCUMENTS

| | | |
|---|---|---|
| 5,498,083 | 3/1996 | Brown . |
| 5,547,286 | 8/1996 | Struziak . |
| 5,584,582 | 12/1996 | Brown . |
| 5,634,723 | 6/1997 | Agrawal ................................. 384/106 |
| 5,833,369 | 11/1998 | Heshmat . |
| 5,871,284 | 2/1999 | Nadjafi et al. . |
| 5,902,049 | 5/1999 | Heshmat . |
| 5,911,510 | 6/1999 | Saville ................................. 384/106 |
| 5,988,885 | 11/1999 | Heshmat . |

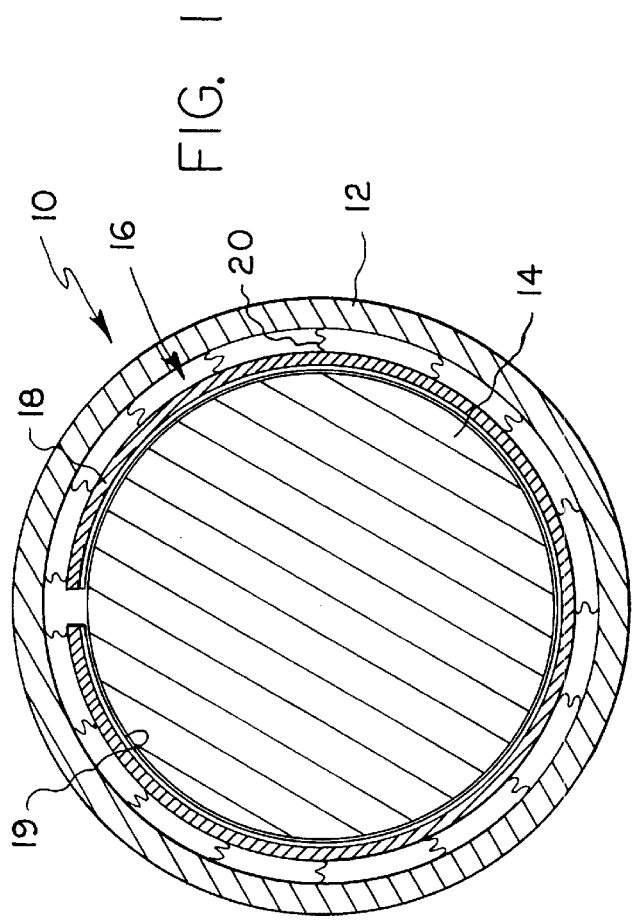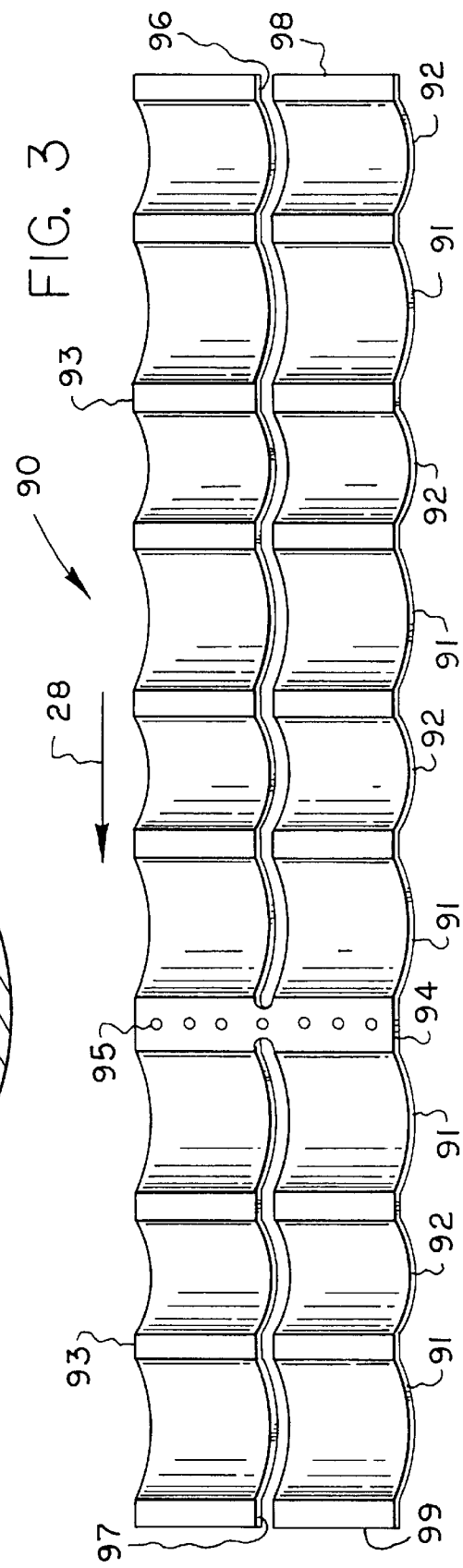

HIGH LOAD CAPACITY COMPLIANT FOIL HYDRODYNAMIC JOURNAL BEARING

This is a division of application Ser. No. 09/234,719, filed Jan. 21, 1999 (U.S. Pat. No. 5,988,885), which is a division of application Ser. No. 08/827,203, filed Mar. 28, 1997 (U.S. Pat. No. 5,902,049), which is incorportated herein by reference.

The present invention relates generally to compliant foil hydrodynamic fluid film journal bearings.

My U.S. patent application titled "High Load Capacity Compliant Foil Hydrodynamic Thrust Bearing," which is filed on even date herewith, is incorporated herein by reference.

Such a bearing includes a smooth foil which is positioned to face a shaft for relative rotation therebetween by means of an air or gas hydrodynamic film therebetween during such rotation. A corrugated sheet is disposed between the smooth foil and a sleeve or bearing housing for compliantly or resiliently supporting the smooth foil, i.e., the bumps or ridges on the sheet deflect under load during shaft rotation. The elastic deflection of the sheet provides the clearance geometry required to generate the load-carrying hydrodynamic film.

Examples of compliant foil hydrodynamic journal bearings are found in my prior U.S. Pat. Nos. 4,262,975; 4,465,384; and 4,300,806 and in U.S. Pat. Nos. 3,809,443; 4,229,054; and 4,274,683. These patents disclose features and teachings which may be incorporated in the bearings described in this application and are therefore incorporated herein by reference.

Additional examples of compliant foil hydrodynamic journal bearings are found in U.S. Pat. Nos. 4,295,689; 4,415,281; 4,435,839; 4,451,163; 4,475,824; 4,552,466; 4,950,089; 5,116,143; 5,228,785; 5,498,083; and 5,584,582 which are also incorporated herein by reference.

Other art which may be of interest includes U.S. Pat. Nos. 3,809,443; 4,277,113; 4,699,523; 5,110,220; 5,248,205; 5,318,366; and 5,547,286.

In foil bearings, the clearance geometry required to generate load-carrying hydrodynamic films is provided by the elastic deflection of the foils. As speed increases, the smooth top foil or sheet and corrugated support foils are automatically forced radially outwardly, forming a converging wedge. Thus, the optimum shape for hydrodynamic action is formed without having to use complex and expensive machining. Furthermore, the converging effects become more pronounced as a function of speed and load, thereby increasing bearing load capacity. The compliant surface readily accommodates shaft centrifugal growth with minimal loss of load capacity and without increased complexity.

The corrugations of the compliant foil support may be tailored to provide the desired bearing stiffness and damping to meet specific system dynamic requirements. For example, see my paper no. AIAA-91-2102 entitled "Analysis of Compliant Foil Bearings with Spatially Variable Stiffness," given at the AIAA/SAE/ASME/ASEE 27th Joint Propulsion Conference, Sacramento, Calif., Jun. 24–26, 1991, which is hereby incorporated herein by reference, and my prior aforesaid U.S. Pat. No. 4,300,806. This paper discloses varying stiffness by placing one bump foil over another-bump foil or by varying bump height and using multi-layered top smooth foils or by varying the thickness, pitch, etc. of the foils.

Foil bearings are used in a variety of rotating machinery. More particularly, foil bearings are suitable for high-speed machines such as cryogenic turbo-rotors with both expander and compressor wheels running at tens of thousands of rpm and much higher. These bearings may also be used in the presence of liquid or cryogens or mixed-phase lubrication. In these applications, the bearing's compliance and potential low cost are advantageous. The use of the foil bearing in aircraft air cycle machines (ACMs) for pressurization and cabin cooling is considered to be the most meaningful and successful application since the late 1970s. In this application, foil bearings have achieved long service life with no scheduled maintenance as well as avoiding cabin contamination by eliminating the oil lubrication system required by conventional ball bearings. The forgiveness of the foil bearing relative to the rolling element bearing in minimizing damage to aerodynamic components in the event of a system malfunction has also been demonstrated. For example, a three-wheel ACM, which utilizes hydrodynamic foil bearings, is currently in use on Boeing 747 aircraft in transatlantic service. The foil bearings in this ACM have accumulated more than one million flight hours and have demonstrated a mean time between failures in excess of 100,000 hours.

Bearings in certain military aircraft such as fighters must meet the additional requirements of very high speed and severe gyroscopic moments with compact construction (i.e., light weight, smaller rotor, and high ambient temperatures). Furthermore, optimal output power and efficiency of brushless electric motors/generators are realized at higher speeds, in the range beyond 60,000 rpm. Conventional bearings are considered to be incapable of meeting those speeds and operating conditions. As a result, it is considered desirable that foil bearings be used with these motors. However, the motor-driven compressor system and turbo-alternators put stringent demands on the application of these bearings. Foil bearings in these systems must have the ability to accommodate misalignment, rotor vibrations, shock loading, centrifugal growth, and elastic and thermal distortions.

Integration of compliant foil gas bearings into turbochargers is also eagerly pursued since they may address and eliminate many problems associated with current turbochargers, such as oil coking during high temperature operation and heat soak-back, the need for auxiliary water cooling jackets, operating speed limitations, and environmental pollution. However, in order to successfully integrate foil bearings into oil free turbochargers and similar machines, it is considered necessary that the foil bearings be able to operate at high temperatures and high speeds, i.e., about 1200 degrees F. at speeds above about 100,000 rpm with a greater damping capacity.

The maximum load capacity of foil journal bearings in air at 70 degrees F. and 14.7 psia has been about 50 psi at a speed of 60,000 rpm. See the paper given by myself, W. Shapiro, and S. Gray entitled "Development of Foil Journal Bearings for High Load Capacity and High Speed Whirl Stability," Trans. ASME, *J. Lubr. Tech.*, vol. 104, no. 2 (April 1982):149–156. This paper discloses a foil bearing wherein, to enhance load capability, the supporting bump foil was split circumferentially along the axial length of the bearing to provide improved alignment and axial compliance of the bearing.

It is considered desirable to provide improved foil bearings which will have increased load capacity, i.e., 100 psi or more, at high speeds of perhaps 60,000 rpm or more while being subjected to high temperatures of perhaps 650 degrees C. or higher. Such increased capacity bearings may have application in pumps, auxiliary turbo-compressors, high speed drills (dental, circuit boards, and others), high speed rotary scanning systems, refrigeration compressors, turboexpanders, large turbochargers for diesel engines, centrifuge pumps for gas, vapor, and liquids, and other applications.

The stiffness, which has been required of the top smooth sheet to prevent its sagging between the bumps of the corrugated foils, undesirably detracts from the ability to manage shaft misalignment and therefore hinders the achievement of high load capacities.

The anchoring of a corrugated foil at one of its ends hinders the achievement of a stiffness profile axially so that an increase in the effective bearing span is hindered.

It is accordingly an object of the present invention to provide a foil with a high load capacity.

It is a further object of the present invention to provide such a bearing for use at high operating speeds and temperatures.

In order to enhance the flexibility of the smooth top foil or sheet in all directions to manage shaft misalignment and excursions thus providing optimal conformity to the bearing surface so that higher load capacities may be achieved, in accordance with the present invention, the top sheet is made very thin, and a second sheet is provided to underlie the top sheet to prevent sagging thereof between the ridges of the corrugated foil. The second sheet is provided with slots for heat removal and also acts as a thermal barrier to the passage of frictional heat, generated as the bumps are flexed, to the top smooth sheet. This second sheet perforated with slots is also provided to prevent excessive deflection of the top sheet between the ridges of the corrugated foil.

In order that both ends of a bump foil are unanchored and free so that, in conjunction with indexing of the bump foils and splitting them circumferentially, a greater stiffness profile axially may be achieved so that the effective bearing span may be increased, in accordance with the present invention, the corrugated foils are anchored to the sleeve at points intermediate their ends.

In order to provide a controlled rippling effect at operating speeds so that increased capacity may be achieved, in accordance with the present invention, ends of foil elements are offset circumferentially from ends of foil elements in adjacent rows thereof symmetrically from the radial centerplane of the bearing assembly to provide a herringbone pattern.

In order to achieve three levels of stiffness for increased capacity, in accordance with the present invention, the bearing assembly has radially outer and inner bump foils wherein outer foil ridges underlie only some (not all) of the inner foil ridges.

In order to prevent the inner and outer bump foils from locking up during flexing thereof and thereby cause drastic increase in stiffness and perhaps permanent deformation, in accordance with the present invention, at least some of the ridges on at least one of the bump foils have truncated apex portions.

The above and other objects, features, and advantages of the present invention will be apparent in the following detailed description of the preferred embodiments thereof when read in conjunction with the accompanying drawings wherein the same reference numerals denote the same or similar parts throughout the several views.

BRIEF DESCRIPTION OF THE DRAWINGS

FIG. 1 is a schematic view taken in a radial plane of a journal bearing which embodies the present invention.

FIG. 3 is a plan view of an alternative embodiment of a foil element therefor, shown unwrapped, i.e., before it is curved into an arcuate shape for installation in the bearing assembly.

FIG. 13 is a schematic plan view, unwrapped, of an alternative embodiment of a foil assembly.

DETAILED DESCRIPTION OF THE PREFERRED EMBODIMENT

Figure 2:
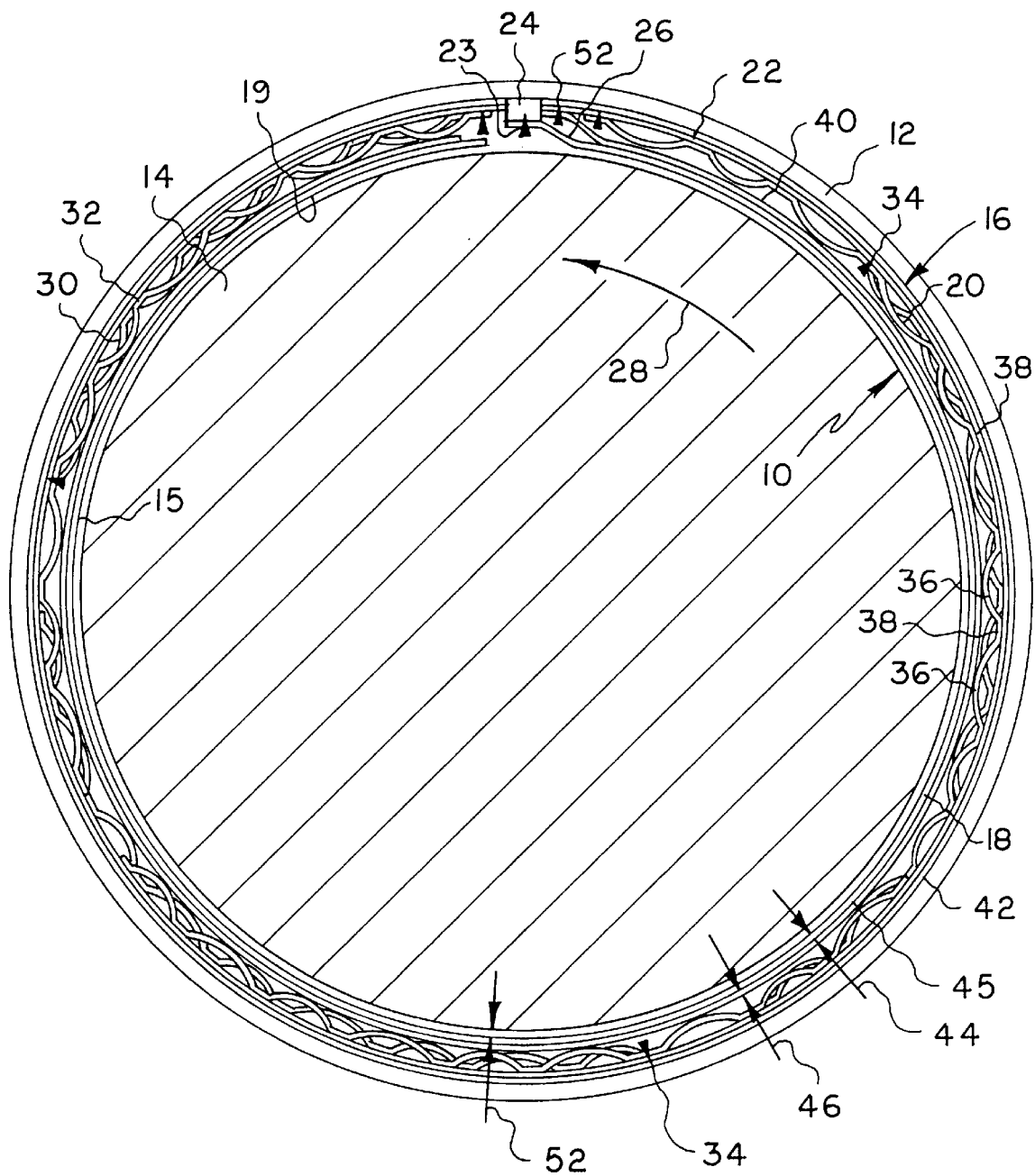
FIG. 2 is an end view thereof, with the shaft in section.

Referring to FIG. 1, there is illustrated generally at 10 a journal bearing which includes a cylindrical housing or sleeve 12 for receiving an elongate rotor or shaft 14 for relative rotation therebetween. While the shaft 14 and housing 12 are shown to be cylindrical, it should be understood that they may be otherwise shaped, such as conical, and the other components of the bearing suitably shaped to be compatible with such alternative shapes, which are meant to come within the scope of the present invention. While typically the shaft 14 will rotate within the stationary bearing 10, the present invention is meant to include embodiments wherein the sleeve 12 rotates with respect to the shaft 14 or where there is rotation of both the shaft 14 and sleeve 12. Suitably mounted to the housing 12 so as to be non-rotatable and disposed in the annular space between the housing 12 and shaft 14 is a foil bearing assembly, illustrated generally at 16. The bearing assembly 16 comprises a smooth compliant sheet 18 which faces the shaft 14, i.e., its radially inner surface 19 serves as the bearing surface for supporting the relatively rotating shaft 14. As used herein and in the claims, unless otherwise specified, the terms "radial" and "radially" are meant to refer to distance or relative position from the shaft 14. A foil assembly 20, described hereinafter and illustrated schematically in FIG. 1 as springs spaced circumferentially about the bearing, is disposed between the compliant sheet 18 and the sleeve 12 to allow the compliant sheet 18, when loaded, to deflect, producing (as in a conventional elastohydrodynamic bearing) a film thickness higher than that of an equivalent rigid surface. During operation, the bearing surface 19 and shaft are separated by a gaseous film, i.e., the shaft rides on a soft cushion of air or a suitable fluid which is introduced so that, under normal operating conditions, wear of bearing surfaces is eliminated.

During start-up and at low speeds, the shaft 14 will ride and rub directly on the compliant sheet 18. In order to suitably reduce friction during these times, a high temperature dry film coating, illustrated at 15 in FIG. 2, is applied to the radially inner shaft engaging surface 19 of the compliant sheet 18. For most ambient air and temperature applications and for the cryogenic environment, coatings which are considered desirable for coating 15 include soft coatings such as, for example, polyamide-imide, PTFE or molybdenum disulfide, or tungsten disulfide. These coatings, which are considered to provide good wear protection during start-up, shut-down, and high speed rubs, are generally applied via air brush or air spray onto the surfaces to be coated, suitably cured, and burnished using abrasive papers to achieve a smooth finish. The shaft 14 (runner surface) may be similarly coated or may be coated with a hard coating such as, for example, nickel plating or a carbide coating. For bearings for high temperatures up to about 815 degrees C., plasma sprayed wear resistant coatings may be used. To achieve smooth surfaces for plasma sprayed coatings, they are suitably ground and lapped after application. It may be desired to apply hard sputtered coatings on the smooth compliant sheet 18 and plasma spray coatings on the shaft 14. In some applications, such a coating may not be considered necessary.

Referring to FIG. 2, the bearing assembly 16 includes, in addition to the compliant sheet 18, a radially outer cartridge sheet 22 which is tack or spot welded or otherwise suitably fixedly attached to the sleeve 12. Spot or tack welded, as illustrated at 23, or otherwise suitably attached to a spacer block 24, which is suitably attached to the sleeve 12, such as by tack or spot welding, is the trailing edge 26 of compliant sheet 18. The direction of rotation of shaft 14 is illustrated at 28. In order that the sheet 18 may be compliant to shaft rotation, it is not otherwise attached but is allowed to freely "float". The foil assembly 20 is shown to include one or more such as a pair of side-by-side corrugated foils 30 and 32 which extend circumferentially of the bearing assembly 16 and are anchored to the cartridge sheet 22 such as by spot or tack welds, illustrated at 34, spaced circumferentially of the bearing assembly 16.

Figure 14:
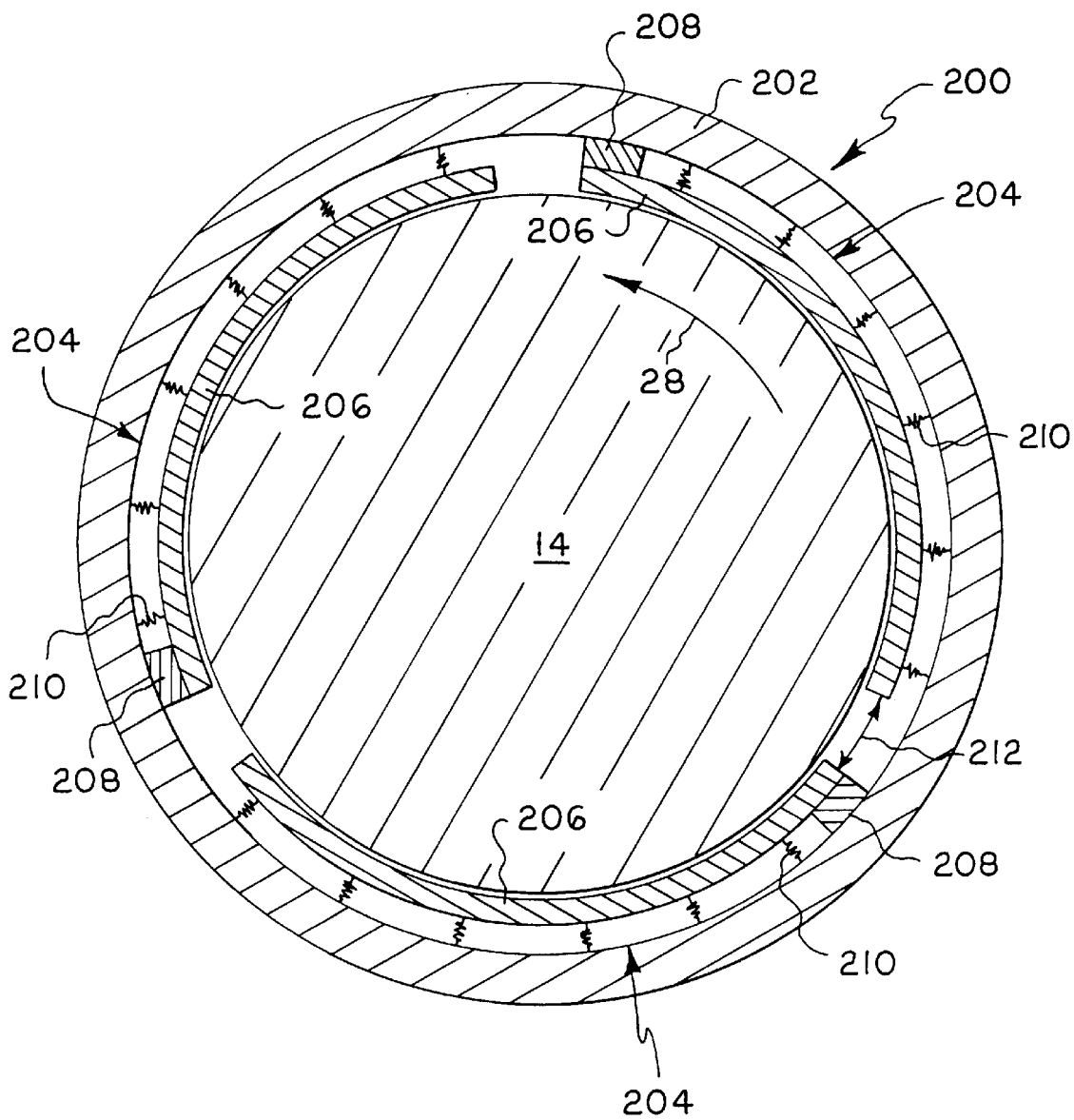
FIG. 14 is a view similar to that of FIG. 1 of an alternative embodiment of the present invention.

While the bearing assembly 16 is shown to comprise a single compliant sheet 18 and single corrugated foils 30 and 32 each of which extends substantially entirely around the bearing circumference, it should be understood that the present invention is meant to alternatively include multiple assemblies of compliant sheets and corrugated foils with each assembly extending over a predetermined arc of the bearing circumference so that the multiple assemblies together provide the bearing surface 19. Thus, FIG. 14 illustrates generally at 200 an alternative journal bearing which may incorporate the present invention. Mounted to the housing or sleeve 202 are three bearing pad assemblies 204 separated circumferentially by a gap, illustrated at 212, of about 2 to 5 degrees of arc wherein each of the bearing pad assemblies 204 covers generally about 115 to 118 degrees of the sleeve circumference. Each bearing pad assembly 204 includes a smooth compliant sheet 206 similar to sheet 18. The trailing edge of each sheet 206 is tack or spot welded or otherwise suitably attached to a spacer block 208 so that the leading edge portion thereof may freely "float." The spacer block 208 is in turn tack or spot welded or otherwise suitably attached to the sleeve 202 similarly as discussed for bearing 10. Together, the compliant sheets 206 provide the needed bearing surface about the shaft 14. A foil assembly 210, similar to foil assembly 20, is suitably provided to underlie each compliant sheet 206. It should of course be understood that a bearing in accordance with the present invention may contain any suitable number of such pad assemblies 204.

Each of the corrugated foils 30 and 32 has a series of circumferentially spaced bumps or ridges 36 upon which the compliant sheet 18 is resiliently supported (as more particularly described hereinafter) and a series of furrows 38 between the ridges. It should be understood that embodiments wherein the ridges face radially outwardly toward the cartridge sheet 22 as well as radially inwardly toward the compliant sheet 18 are meant to come within the scope of the present invention. As seen in FIG. 2, the furrows 38 may comprise generally flat portions which engage the cartridge sheet 22. The bumps 36 are semicircular or otherwise suitably arcuate in shape (for example, sinusoidal) so that they flex under load to provide compliant support (in the nature of a spring, as illustrated in FIG. 1) for the smooth compliant sheet 18.

The corrugated foils 30 and 32 as well as the compliant sheets 18 are desirably composed of metal or, for some applications, thermoplastic material, which material is fatigue-resistant, has good spring properties, and has strong mechanical strength. For example, the corrugated foils and sheets may be composed of nickel-based steel or a beryllium-copper or beryllium-bronze alloy. For another example, the sheet 18 may be composed of constrained layers (multi-layer composite material) providing good damping (i.e., internal damping).

Many ways are well known, by those of ordinary skill in the art to which this invention pertains, for manipulating the sizes and shapes of the bumps 36 and for positioning them relative to bumps on other foils to achieve the bearing stiffness and damping needed to meet specific system dynamic requirements. Thus, FIG. 2 illustrates offsetting circumferentially of the bumps 36 in the foil 30 from the bumps 36 in the foil 32. Since the principles for design of foils 30 and 32 are within the knowledge of one of ordinary skill in the art to which this invention pertains, the design of these particular foils 30 and 32 will not be described further.

In order to adjust the bearing stack-up height in order to achieve the desired final nominal bearing clearance, illustrated at 52, between the compliant sheet 18 and the shaft 14, which may be desirably in the range of about 0.0001 to 0.0002 inch, one or more thin foil shims 42, as needed, is rolled and placed between the sleeve 12 and cartridge sheet 22 just prior to anchoring the bearing assembly to the sleeve 12, either mechanically or via tack welds.

In order to enhance the flexibility of the smooth compliant sheet 18 in all directions to manage shaft misalignment and excursion and thereby provide optimal conformity to the bearing surface, the compliant sheet 18 is selected to be a very thin foil. However, such a very thin sheet may have a tendency undesirably to sag between the bumps 36. In order to prevent such a sagging tendency, in accordance with the present invention, the very thin compliant sheet 18 is supported by an underlying sheet 40 to provide structural integrity and preloading for preventing undulation of the compliant sheet surfaces or rippling thereof. The combination of the compliant sheet 18 and support sheet 40 is also provided to make the compliant sheet 18 act stiff in the circumferential direction but very resilient in the axial direction.

For example, for a conventional dental drill bearing, the compliant sheet may have a thickness of perhaps about 2.5 mils. By adding a support sheet having a thickness, illustrated at 46 in FIG. 2, of perhaps about 0.2 mils in accordance with the present invention, the compliant sheet thickness, illustrated at 44 in FIG. 2, may be reduced to perhaps about 0.3 mils. For another example, for a conventional bearing having a 2 inch length and a 2 inch diameter and lubricated with a liquid having a viscosity of 10 centipoise, the compliant sheet may have a thickness of perhaps about 0.2 inch. By adding a support sheet 40 having a thickness 46 of perhaps about 0.008 inch, the thickness 44 of the compliant sheet 18 may be reduced to perhaps about 0.025 inch. These and other examples contained herein are for illustrative purposes only and not for purposes of limitation.

The side 45 facing the support sheet 40 may be coated, for example, with gold, silver, copper, or other suitable thermally conductive material for distributing localized heat efficiently over its entire surface and effectuate thermal conduction. High frictional metal or metal oxides may alternatively be used as a coating in order to increase frictional damping characteristics of the bearing (frictional losses due to rubbing action between the top foil 18 and the support sheet 40.

Figure 9:
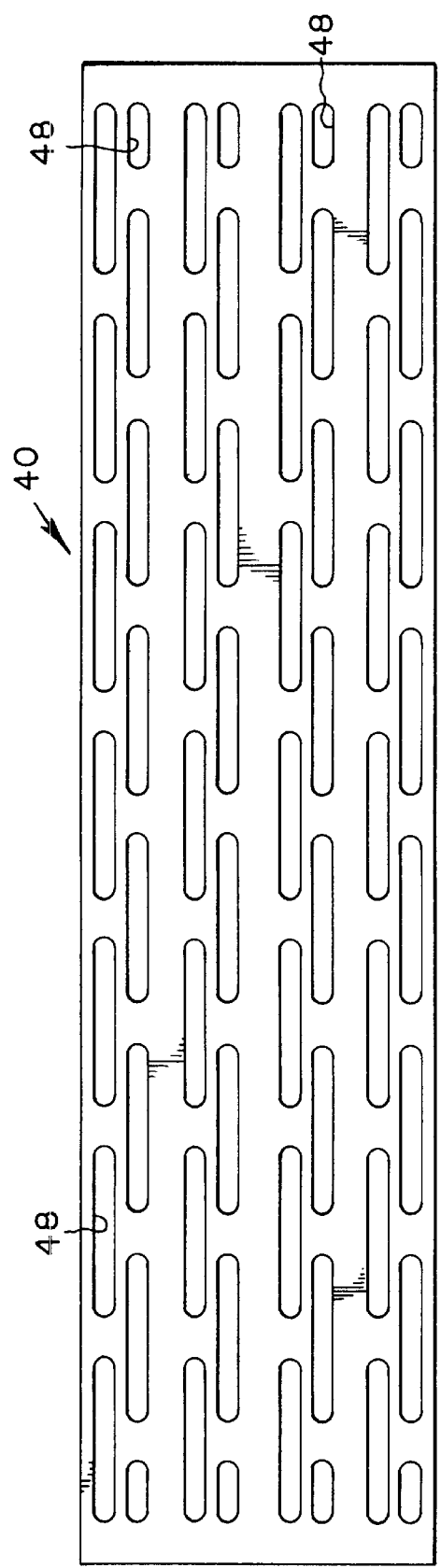
FIG. 9 is a plan view, shown unwrapped, of a thermal barrier sheet for the bearing assembly of FIGS. 2 and 5.

Referring to FIG. 9, further in accordance with the present invention, the support sheet 40 is perforated with a plurality of slots, illustrated at 48, so as to allow ambient air cooling flow to, as well as supporting of, the compliant sheet 18. Axial cooling flow in the form of gas or liquid or process fluid may also be passed through these slots 48 to even more effectively remove heat from the compliant sheet 18. More specifically, sources of heat generation in the bearing 10 include shearing of the solid thin film dry coating 15 by the shaft 14 during start-up and shut-down, shearing of the fluid film during normal high speed operation, and rubbing between apexes of the bumps 36 on adjacent foils or sheets. The thermal barrier sheet 40, in addition to acting as a heat exchanger device to the compliant sheet 18, is also provided to act as a thermal barrier against frictional heat that is generated between the bumps 36, the compliant sheet 18, and itself. The thermal barrier sheet 40 is preferably composed of a good thermal conductivity material which may be similar to the material of which top compliant sheet 18 is composed and may be provided on its radially inner and outer surfaces with a thin surface coating such as, for example, gold, silver, copper, or other suitable material to further its effectiveness as a heat sink and damping enhancer. After it is rolled, the trailing end of the thermal barrier sheet 40 is anchored adjacent the spacer block 24 to the cartridge sheet 22 by means of spot welds, illustrated at 52, and the other end thereof is free. The slots 48 provide additional flexibility to further aid in compensating for shaft misalignment and excursion.

Figure 4:
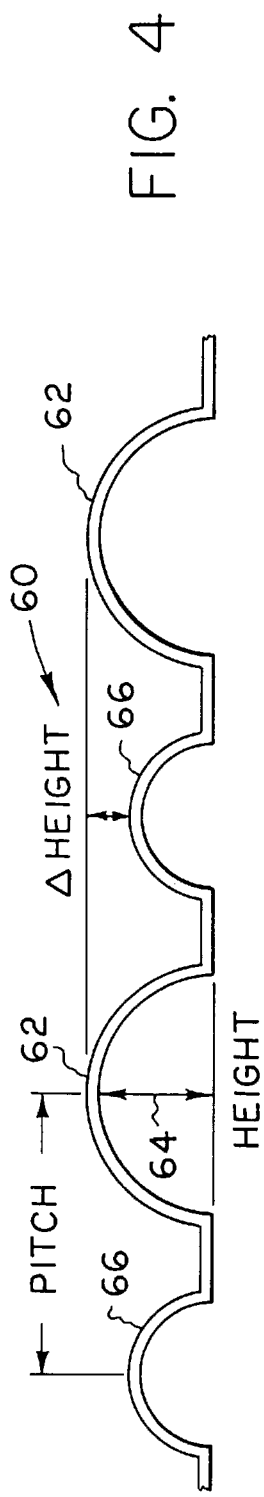
FIG. 4 is a partial side view, illustrated unwrapped, of another embodiment of a foil element therefor.
Figure 6:
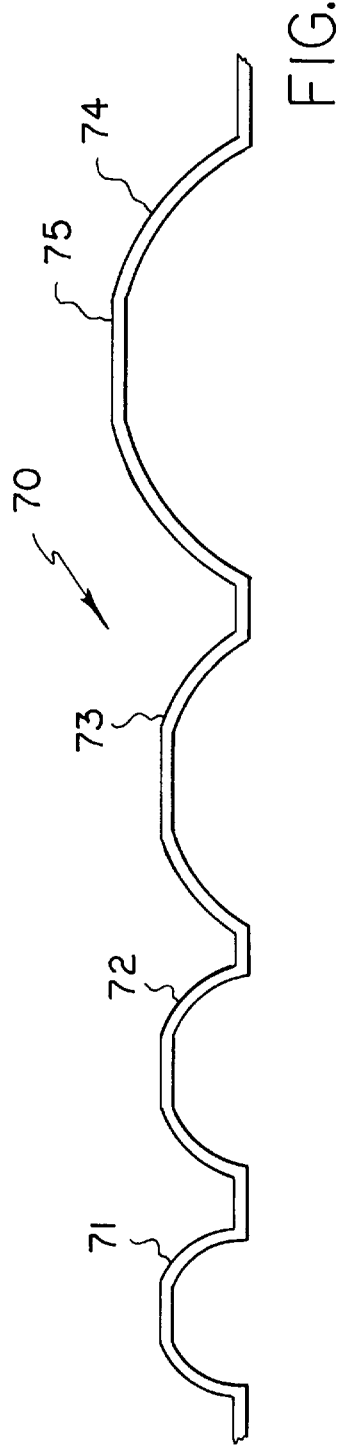
FIG. 6 is a view similar to that of FIG. 4 of another embodiment of a foil element therefor.

Referring to FIGS. 4 and 6, as previously discussed, the sizing and shapes of the bumps 36 may be tailored and variegated (varying the sizes and shapes over the foil circumference) in order to achieve the desired bearing stiffness and damping to meet specific system dynamic requirements. Further, upper and lower corrugated foils having bumps of longer pitches underlying shorter pitch bumps have been employed. As seen in FIG. 4, a single bump foil strip 60 has bumps 62 of greater height, illustrated at 64, and length alternating with bumps 66 which have a lesser height and length. Under light load, the larger bumps 62 are in contact with the smooth compliant sheet or sheets 18. As the applied load increases, the larger bumps 62 deflect causing the smaller bumps 66 to also contact the compliant sheet or sheets 18 to thus provide a desired higher stiffness at higher loads.

Figure 7:
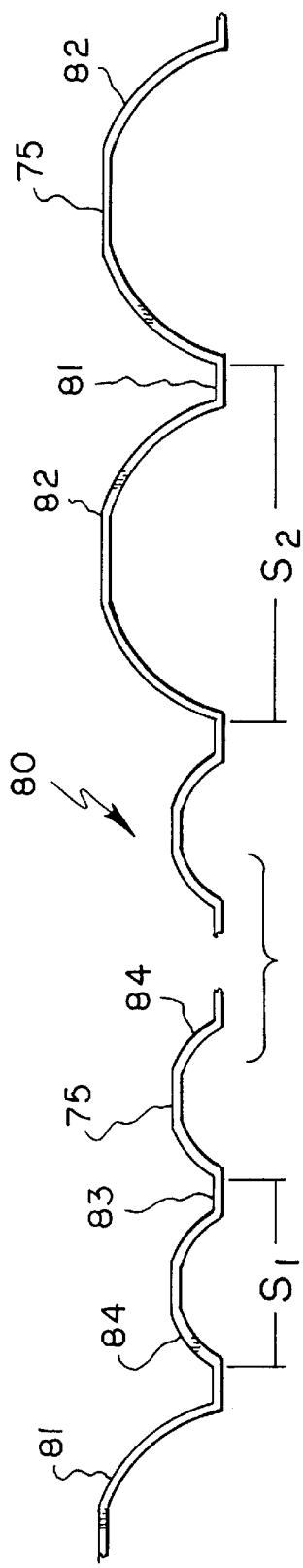
FIG. 7 is a view similar to that of FIG. 4 of yet another embodiment of a foil element therefor.

FIG. 6 illustrates a bump foil portion 70 having bumps 71, 72, 73, and 74 with successively increasing heights and lengths in order to vary stiffness gradient circumferentially along the bump strip. FIG. 7 illustrates a bump foil 80 having portions 81 with bumps 82 having large heights, lengths, and pitches, illustrated at S2, alternating with portions 83 with bumps 84 having smaller heights, lengths, and pitches, illustrated at S1.

Figure 8:
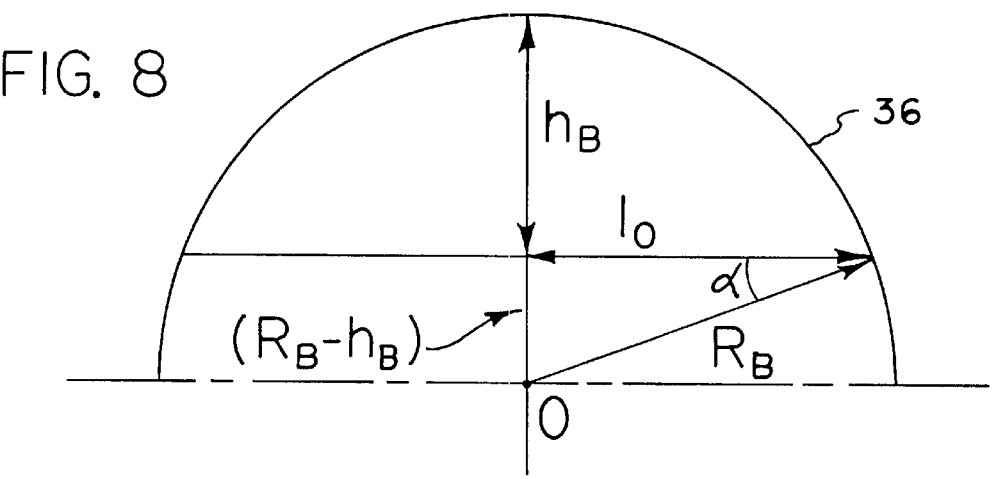
FIG. 8 is a schematic of a foil element bump for the purpose of illustrating geometric relationships.

Referring to FIG. 8, a bump foil strip stiffness may be derived as follows:

$$\cos \alpha = l_0/R_B \qquad \alpha = \arccos(l_0/R_B)$$
$$\sin \alpha = (R_B - h_B)/R_B \qquad h_B = -R_B \sin \alpha + R_B$$
$$h_B = R_B - R_B [\sin(\arccos(l_0/R_B))]$$
$$l_0 = R_B \cos[\arcsin((R_B - h_B)/R_B)]$$
$$K_{BS} = [6Et^3/12(1 - v_B^2)/l_0^3 S]$$

where $K_{BS}$ is the bump foil strip stiffness, E and $V_B$ are material properties (Modulus of Elasticity and Poisson's Ratio respectively), t is bump foil thickness, $l_0$ is half of the bump length, and S is bump pitch. Note that $l_0$ is strongly related to bump radius and weakly related to bump height $h_B$.

Stiffness of a bump strip is strongly proportional to $t^3/l_0^3$ and inversely proportional to the bump pitch S. However, it is a weak function of $h_B$. Therefore, a number of smaller bumps with pitch S may desirably be combined with larger bumps with pitch different than $S_1$, i.e., $S_2$ (FIG. 7).

Furthermore, variable $l_0$ may desirably be used to obtain variation on stiffness, as seen in FIG. 6.

Figure 5:
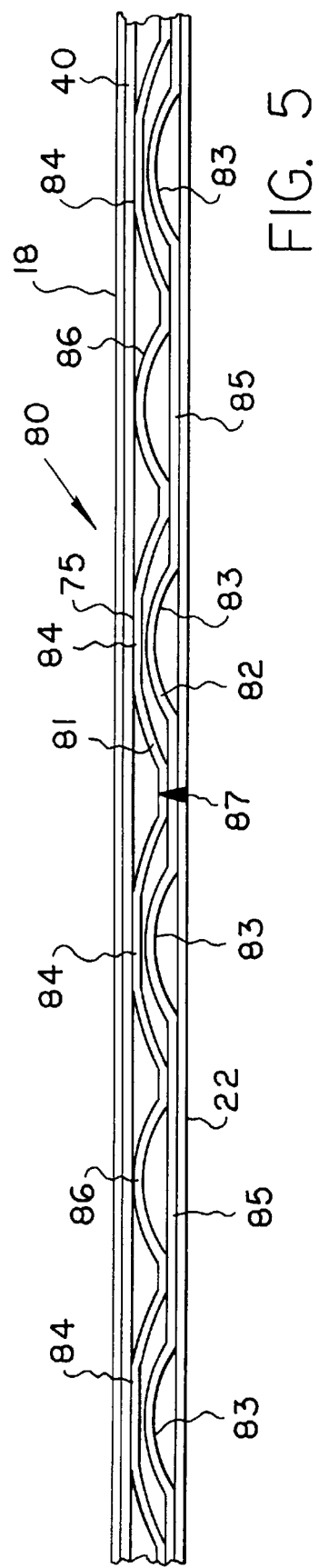
FIG. 5 is a partial side view, illustrated unwrapped, of an alternative embodiment of a bearing assembly therefor.

Referring to FIG. 5, there is shown a bearing assembly 80 which has inner and outer corrugated foils 81 and 82 respectively. Inner foil 81 has a plurality of bumps of relatively greater height and length. Outer foil 82 has a plurality of bumps 83 of lesser height and length to underlie inner sheet bumps with a relatively large pitch S. In order to provide three or more levels of stiffening so as to provide an isolation feature to the bearing assembly 80 thus increasing its shock loading capacity, in accordance with the present invention, outer foil bumps or ridges 83 underlie some 84 of the inner foil bumps or ridges while relatively long segments of flat portions or furrows 85 underlie others 86 of the inner foil bumps. Under moderate load, there is a clearance between the peaks of the outer foil bumps 83 and the corresponding inner foil bumps 84 whereby the load is supported with minimum rigidity by only the inner foil bumps 84 and 86. As load is further applied, it initially only deflects the inner bump foil 81 until the load is sufficient to bring the two bump foils 81 and 82 into contact. Continued increase of the load causes both bump foils 81 and 82 to deflect increasing the stiffness over the bumps 84 but wherein there is still minimal stiffness over the bumps 86.

When the inner and outer bumps are deforming radially together, they undergo some circumferential displacement to achieve the desired stiffness and damping characteristics. However, if the bumps have perfect semi-circular shapes, they will have a tangential line contact, and one such arcuate bump inside another such arcuate bump may not easily move longitudinally (circumferentially), i.e., the bumps may lock up resulting in drastic increase in their stiffness, and they may deform permanently. In order to prevent such a tangential line contact so as to accommodate sliding of the inner foil bumps, the bumps 84 of the radially inner foil 81 have flat or truncated top or apex portions, illustrated at 75 in FIG. 5 as well as in FIG. 6. By "apex portion" is meant, for the purposes of this specification and claims, the outermost portion of a bump, i.e., the portion which engages a sheet or foil such as support sheet 40 or, if the bearing does not have such a support sheet, compliant sheet 18. Alternatively, the outer foil bumps 83 may instead have truncated apex portions, or the bumps of both foils may have truncated apex portions.

Referring to FIG. 3, there is shown generally at 90 an elongate corrugated strip foil with variegated bumps, i.e., alternately (except as noted hereinafter) longer and higher bumps 91 and bumps 92 which are not as long and high, and with flat portions or furrows 93 therebetween for engaging the cartridge sheet 22. In order that both ends of the foil strip 90 may be free (unanchored) for purposes which will be discussed hereinafter, in accordance with the present invention, the foil strip 90 has a portion 94 intermediate its ends which is spot welded, as illustrated at 95, to the cartridge sheet 22. Adjacent each side of portion 94 is one of the longer and higher bumps 91 for attenuating the rigidity provided by the anchoring of the portion 94.

Portion 94 is preferably positioned at about ⅓ of the total length of the bump foil strip relative to the trailing end 99 in order to provide graduating parabolically shaped stiffness gradient over the bump foil strip (i.e., stiffness gradually increases from leading end 98 of the bump strip approaching its maximum level over the bumps adjacent portion 94 then gradually decreases toward trailing end 99 ). Such a parabolically shaped gradient is considered desirable to optimally achieve a gap, discussed in my aforesaid U.S. Pat. No. 4,277,112, between the complient sheet 18 and the shaft which is wedge shaped, tapering in the direction 28 of shaft rotation. The pressure of the fluid drawn into the wedge shaped gap tends to increase toward the narrow end of the gap thus creating the pressurized cushion of fluid film which dynamically supports the rotating shaft. Thus, as each individual bump gets closer to the spot weld zone 94 (from either end of the strip), its stiffness increases relative to those bumps which are farther away from the spot weld zone. This is considered to be due to an interlocking relationship with adjacent bumps, since the adjacent bumps to the spot weld zone have the highest stiffness relative to the other bumps in the bump strip.

Foil 90 has a pair of longitudinal slits 96 and 97 extending from portion 94 to the leading and trailing ends 98 and 99 respectively and, on each side of portion 94, dividing or severing the respective strip portion into two generally equal elongate segments to thereby reduce variability of stiffness axially along each of the bumps 91 and 92.

Foil members 81 and 82 in FIG. 5 are similarly anchored to the cartridge sheet 22 at a position intermediate their ends by spot welds illustrated at 87 and may also have slits similar to slits 96 and 97. An outer foil bump 83 underlies each of a pair of inner foil bumps 84 which are adjacent each spot weld 87 so as to afford a higher stiffness level adjacent the spot welds 87 in order to attenuate the rigidity resulting from the spot welds 87.

As previously discussed, the shaft does not lift off of the foil bearings when at rest or at low speeds. Instead the shaft rubs against the compliant sheet surface 19. The resulting wear of the compliant sheet and the shaft may be reduced by the use of the rub resistant coating 15, generation of conformal surfaces, and the provision of longer bearings. By also providing uniform load distribution in the axial direction, as illustrated at 100 in FIG. 12, the contact area is increased to thus reduce contact stress and thereby reduce wear of the shaft 14 and compliant sheet surface during start-up, shut-down, and other low speed operations. Since the axial pressure profile is fairly uniform when there is uniform load distribution in the axial direction, the bearing span at low speed conditions is generally equal to that of the bearing geometrical span (distance between centers of gravity of the bearings), illustrated at 102.

Figure 10:
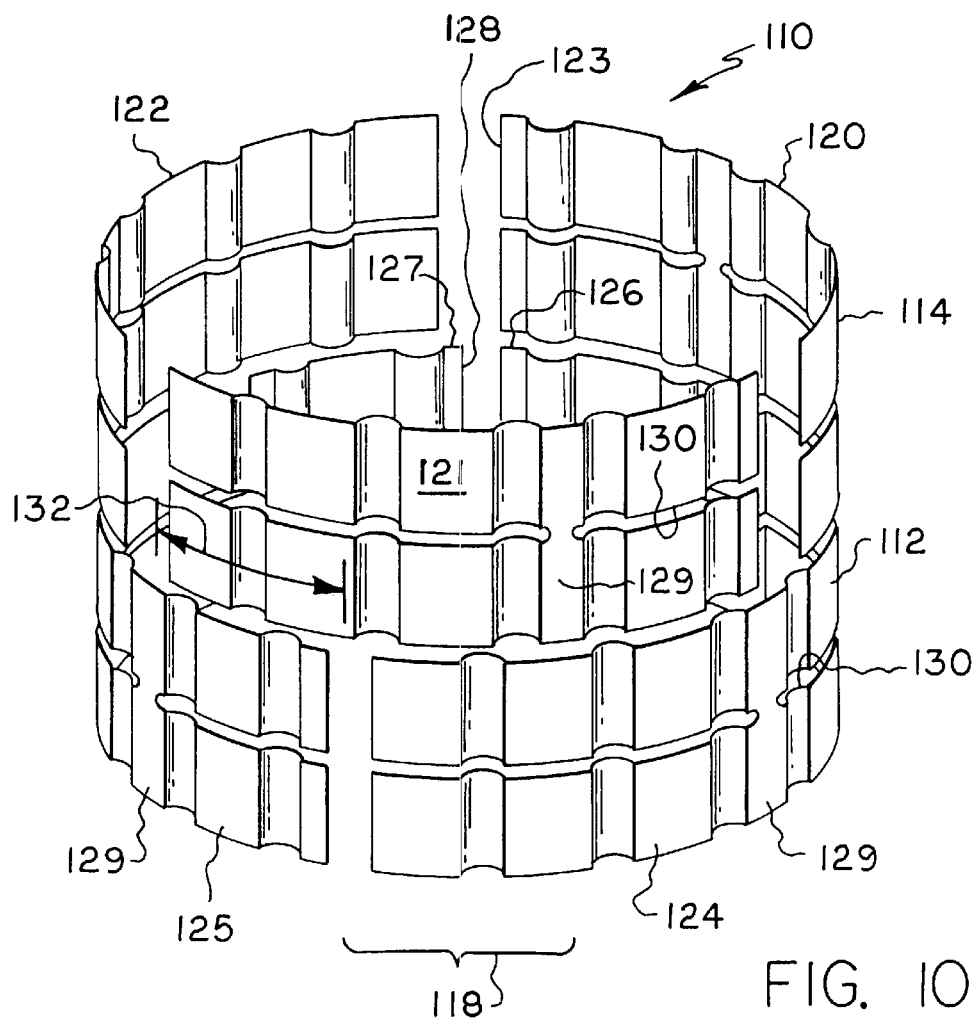
FIG. 10 is a perspective view, wrapped, of an alternative embodiment of an assembly of a plurality of foil elements.
Figure 11:
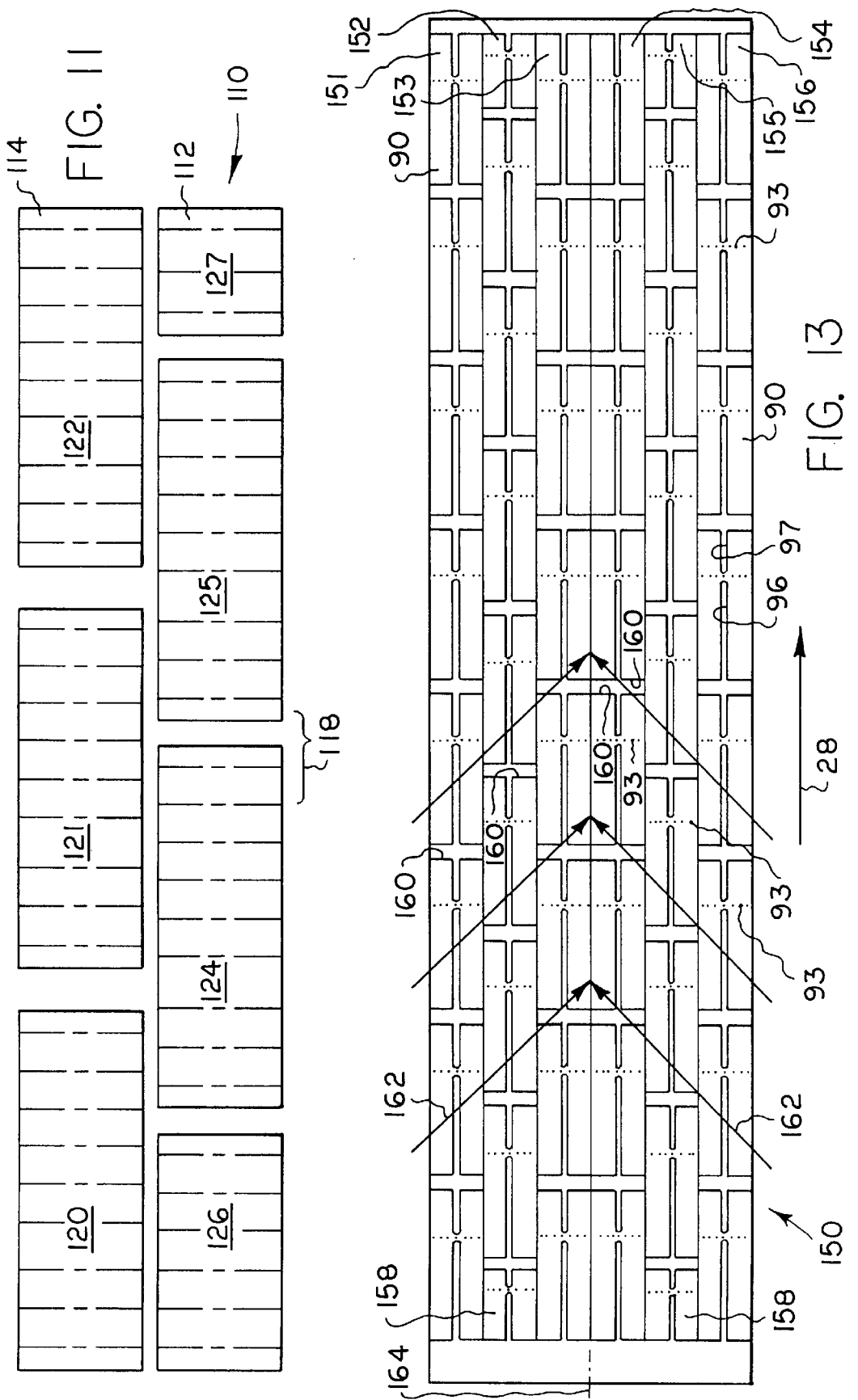
FIG. 11 is a schematic plan view, unwrapped, of the assembly of FIG. 10.

At high speeds when it is no longer necessary to have such uniform load distribution to decrease wear, it is instead desirable to have increased bearing span so that the system operation may be more stable. Bearing span can be increased by providing a longer bearing or shaft. However, this undesirably results in an increase in static load (start-up load). Referring to FIGS. 10 and 11, in order to provide uniform load distribution at low speeds while also providing increased effective bearing span at high speeds, in accordance with the present invention, a corrugated foil assembly 110 is provided wherein two (or more) rows, i.e., an inboard row 112 and an outboard row 114, of corrugated foils are indexed (leading ends staggered so that the foils in one row overlap the foils in the other row), as described hereinafter, so that the lower bearing portion, illustrated at 118, on which the shaft rests while at rest and toward which the shaft bears due to gravity during high speeds has a greater stiffness on the outboard row 114 than on the inboard row 112 of corrugated foils.

The outboard row 114 has three corrugated foils 120, 121, and 122 of equal length and having gaps therebetween at 120-degree intervals around the circumference thereof including one gap 123 at an upper portion of the bearing assembly defined by the two ends of the bearing assembly coming together. The inboard row 112 has two corrugated foils 124 and 125 of equal lengths to foils 120, 121, and 122 and a pair of end corrugated foils 126 and 127. Gaps are provided between these foils, and the lengths of foils 126 and 127 are selected to provide a gap 128 which aligns with gap 123 so that the bearing assembly can be easily assembled with even ends before it is rolled and installed.

Each of the corrugated foils 120, 121, 122, 124, 125, 126, and 127, similarly to foil 90 in FIG. 3, has a portion 129 intermediate its ends for tack welding to the cartridge sheet 22 and has longitudinal slits 130 splitting each foil into two independently flexing portions from the anchoring portion 129 to one end and two independently flexing portions from the anchoring portion 129 to the other end.

The outboard foils are indexed (except at the bearing assembly ends, as previously discussed) so that they overlap the inboard foils and the gaps therebetween are spaced circumferentially from the gaps between the inboard foils by an arc, illustrated at 132, of about 60 degrees. However, it should be understood that, in accordance with the present invention, the arc 132 may be any other suitable number of degrees which achieve the desired effect of increasing effective bearing span, and the bearing assembly may include more than two rows of corrugated foils.

Figure 12:
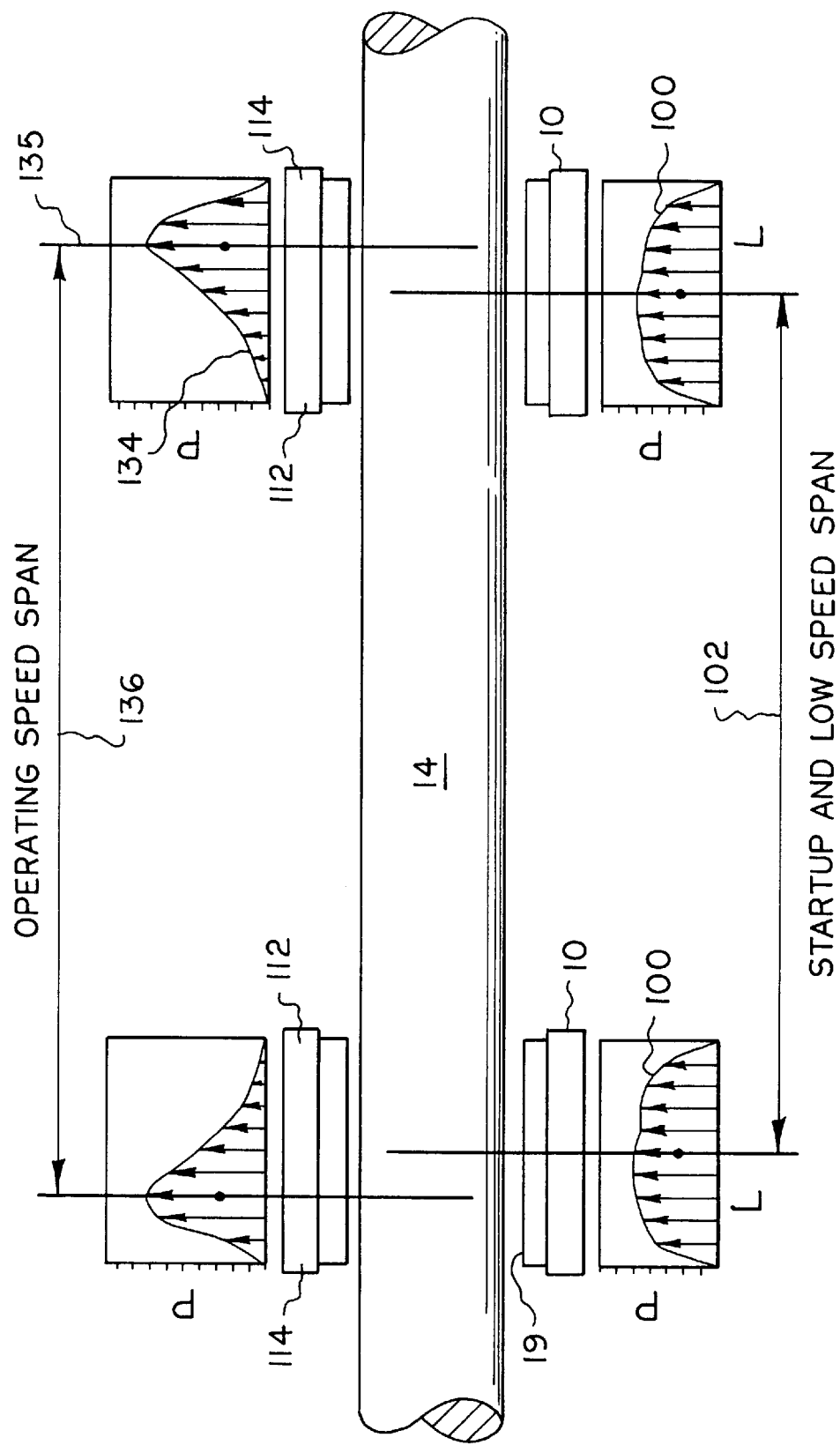
FIG. 12 is a graphic illustration of increased effective bearing span resulting from utilizing the principles of the present invention.

As seen in FIG. 10, the anchor portions 129 of the inboard foils 124 and 125 are spaced a substantial distance circumferentially from lower bearing region 118. An anchor portion 129 of an outboard foil 121, on the other hand, lies substantially within bearing portion 118. Since both ends of each of the foils are free (unanchored), the anchor portions 129 are relatively stiffer than the foil ends, the shapes of the hydrodynamic pressure profiles, illustrated at 134 in FIG. 12, are generally parabolic, and the stiffer the bearing surface, the steeper or greater the hydrodynamic pressure. Thus, with the outboard row 114 providing the greater stiffness in the lower bearing region 118, the shaft 14 "centers" on the outboard row 114 during high speed operation, as illustrated at 135, so that the effective bearing span, illustrated at 136, is desirably increased for operating speed.

Herringbone grooves are built into conventional hydrodynamic bearing and seal surfaces for enhancing these hydrodynamic devices' load capacities. In both journal and thrust bearings with herringbone grooved surfaces, the bearing or runner surface consists of a lattice of grooves and ridges. From a hydrodynamic point of view, the geometry essentially consists of a series of step bearings, although, unlike conventional steps, these are at an angle to the direction of motion. One of the achievements of such a design is that the fluid is being driven away from the edges of the bearing, minimizing side leakage and raising load capacity. By a proper orientation of the grooves, the fluid can be pumped away from either the inner or outer periphery or from both edges. While an ordinary bearing without a herringbone pattern may have poor stability characteristics for a concentric shaft position, the herringbone bearing is considered superior to a conventional bearing at low eccentricities. In addition to the high cost of producing the extremely precise and shallow (in the range of 50 to 100 millionth of an inch deep) groove patterns of herringbone bearings on hard surfaces, maintainability of these tight tolerance surfaces is extremely difficult, and their operational life is jeopardized by the sedimentation of debris and other contaminants borne by the process fluid.

Referring to FIG. 13, in order to provide a herringbone bearing without the disadvantages described above, in accordance with present invention, a bearing assembly is provided which includes a compliant sheet and thermal barrier sheet similar to those shown at 18 and 40 respectively and includes an assembly, illustrated at 150, of a plurality of perhaps 6 rows 151, 152, 153, 154, 155, and 156 of corrugated foils, similar to corrugated foils 90 with anchor portions 93 intermediate their ends and with the split grooves 96 and 97, which are assembled in a staggered or indexed relation, as described hereinafter, to achieve a herringbone effect at high speeds. Rows 151, 153, 154, and 156 are shown to each contain 8 corrugated foils 90 of equal lengths, and each foil extends circumferentially over an arc of about 45 degrees. Rows 152 and 155 each contain 7 corrugated foils 90 of equal lengths to the foils in rows 151, 153, 154, and 156 and staggered or indexed relative thereto so that their free ends are offset by about 22½ degrees from the corresponding free ends of foils in adjacent rows. Their anchor portions 93 are similarly offset by about 22½ degrees from the corresponding anchor portions 93 of foils in adjacent rows. So that all of the rows may have aligned or common ends, rows 152 and 155 have a corrugated foil, illustrated at 158, at each end the length of which is about half the length of the other foils. It should be understood that, in accordance with the present invention, the number of rows of foils, number of foils per row, the types of foils, and the number of degrees of indexing may vary.

As seen in FIG. 13, the gaps 160 between adjacent foils in the two center rows 153 and 154 are aligned (not indexed or staggered relative to each other). In respectively adjacent rows 152 and 155, the gaps 160 are offset or indexed about 22½ degrees upstream from corresponding gaps 160 in rows 153 and 154 respectively. In respectively adjacent outer rows 151 and 156, the gaps 160 are offset or indexed about another 22½ degrees upstream from corresponding gaps in rows 152 and 155 respectively. Thus, a herringbone pattern of gaps, illustrated by arrows 162, which are symmetrical from the radial centerplane, illustrated at 164, of the foil assembly 150 is provided.

At low speed and start-up and shut-down conditions where the hydrodynamic film is ineffective, only global deformation under shaft weight takes place, and the shaft essentially rides on the dry film coating 15 of the conformal surface 19. Once the hydrodynamic pressure/film is fully developed, the compliant sheet 18 along with the thermal barrier sheet 40, under the action of hydrodynamic pressure, will form depressions along the lines 162 of the gaps 160 (which are between lines of rigidity of the anchor portions 93) thereby achieving a herringbone pattern or controlled rippling effect.

Especially for applications such as aircraft gas turbines, a bearing utilizing the corrugated foil assembly of FIG. 13 to achieve a herringbone effect is believed to offer the following benefits. Compared to a conventional herringbone groove bearing, for the same load capacity, this bearing may be smaller, lighter, and may consume less power, and may be more economical. The specific load capacity of this foil bearing may be more than 9,000 lb. per lb. of bearing weight, while that of conventional beerings is typically about 100 lb. per lb. of bearing weight. The rotor may coast down safely on this foil bearing without altering or damaging the groove pattern during start-up and shut-down. This foil bearing surface may smooth out at low speeds or at rest preventing collection of contaminants in the generated grooves. In addition, this foil bearing may withstand a larger static load at low speeds and start-up due to its conforming to the mating surfaces. Sub-synchronous stability may be enhanced by the automatically generated herringbone pattern at higher speeds. Additional damping may be produced by the foil bearing parts with Coulomb friction.

Using principles commonly known to those of ordinary skill in the art to which this invention pertains, one will be able to construct a journal bearing in accordance with the teachings contained herein.

It should be understood that, while the present invention has been described in detail herein, the invention can be embodied otherwise without departing from the principles thereof, and such other embodiments are meant to come within the scope of the present invention as defined by the appended claims.

What is claimed is:

1. A compliant hydrodynamic fluid film bearing comprising a housing for receiving a shaft for relative rotational movement therebetween, a cylindrical bearing assembly adapted to be disposed between said housing and the shaft, said bearing assembly including sheet means positioned to face and surround the shaft for relative rotational movement therebetween, and means for resiliently supporting said sheet means, said supporting means comprising a radially outer foil element means and a radially inner foil element means disposed between said sheet means and said housing, said inner foil element means having a corrugated shape defining a plurality of ridges and a plurality of furrows in alternating relation circumferentially of said bearing assembly for engaging said sheet means, and said outer foil element means having a corrugated shape defining a plurality of ridges and a plurality of furrows in alternating relation circumferentially of said bearing assembly such that outer foil ridges underlie some of said inner foil ridges arm such that outer foil furrows underlie others of said inner foil ridges.

2. A bearing according to claim 1 wherein said some inner foil ridges comprise two of said inner foil ridges which are adjacent said anchoring means and alternate ones of said inner foil ridges from each of said two inner foil ridges to respective ends of said inner foil element means.

* * * * *